(12) United States Patent
Van Daele et al.

(10) Patent No.: US 6,310,077 B1
(45) Date of Patent: Oct. 30, 2001

(54) ENTEROKINETIC BENZAMIDE

(75) Inventors: Georges H. P. Van Daele, deceased, late of Turnhout, by Marie-Louise Hendrickx, heir; by Kurt Godfried Cornelius Emile Van Daele, heir, Borgerhout; by Peter Jules Victor Van Daele, heir, Grimbergen; by Glenn Kurt Ludo Van Daele, heir, Turnhout; Jean-Paul René Marie André Bosmans, Edegem; Joannes Adrianus Jacobus Schuurkes, Beerse, all of (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/325,865

(22) Filed: Jun. 4, 1999

Related U.S. Application Data

(62) Continuation of application No. 09/159,993, filed on Sep. 24, 1998, which is a continuation of application No. 08/836,276, filed as application No. PCT/EP95/04519 on Nov. 16, 1995, now Pat. No. 5,854,260.

(30) Foreign Application Priority Data

Nov. 23, 1994 (EP) .................................................. 94203421

(51) Int. Cl.$^7$ .................................................. A61K 31/445
(52) U.S. Cl. ............................................ 514/320; 546/196
(58) Field of Search .............................. 514/320; 546/196

(56) References Cited

U.S. PATENT DOCUMENTS

| 5,185,335 | 2/1993 | Van Daele et al. ................... 514/243 |
| 5,374,637 | 12/1994 | Van Daele et al. ................... 514/320 |
| 5,854,260 | * 12/1998 | Van Daele et al. ................... 514/320 |

* cited by examiner

Primary Examiner—Dwayne C. Jones
(74) Attorney, Agent, or Firm—Ellen Ciambrone Coletti

(57) ABSTRACT

The present invention is concerned with a novel benzamide of formula (I).

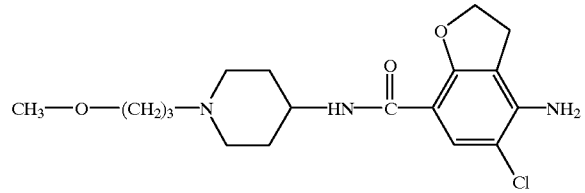

Pharmaceutical compositions comprising said novel compounds, process for preparing compounds and compositions, and the use thereof as a medicine, in particular in the treatment of conditions involving a decreased motility of the intestine are described.

5 Claims, No Drawings

ENTEROKINETIC BENZAMIDE

CROSS REFERENCE TO RELATED APPLICATIONS

This application is a continuation of Application Ser. No. 09/159,993, filed Sep. 24, 1998 which application is a continuation of application Ser. No. 08/836,276, filed Apr. 30, 1997, now U.S. Pat. No. 5,854,260, which is the national stage of Application No. PCT/EP95/04519, filed on Nov. 16, 1995, which application claims priority from EP 94.203.421.6, filed on Nov. 23, 1994.

The present invention is concerned with a novel benzamide derivative and the pharmaceutically acceptable acid addition salts thereof, pharmaceutical compositions comprising said novel compound, processes for preparing said compounds and compositions, and the use thereof as a medicine, in particular in the treatment of conditions involving an impaired motility of the intestine, especially of the colon.

In our EP-0,389,037-A, published on Sep. 26, 1990, N-(3-hydroxy-4-piperidinyl) (dihydrobenzofuran or dihydro-2H-benzopyran)carboxamide derivatives are disclosed as having gastrointestinal motility stimulating properties. In our EP-0,445,862-A, published on Sep. 11, 1991, N-(4-piperidinyl) (dihydrobenzofuran or dihydro-2H-benzopyran)carboxamide derivatives are disclosed also having gastrointestinal motility stimulating properties.

The compound subject to the present application differs therefrom by showing superior enterokinetic properties.

The present invention concerns a compound of formula

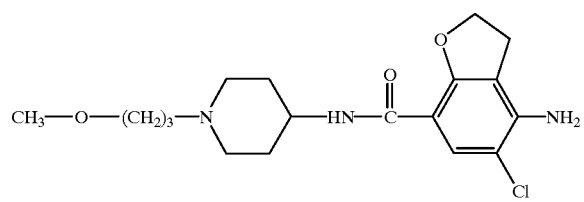

(I)

and the pharmaceutically acceptable acid addition salts thereof.

The chemical name of the compound of formula (I) is 4-amino-5-chloro-2,3-dihydro-N-[1-(3-methoxypropyl)-4-piperidinyl]-7-benzofurancarboxamide.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids: or organic acids such as, for example, acetic, propanoic, hydroxyacetic, lactic, pyruvic, oxalic, malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. The term addition salt as used hereinabove also comprises the solvates which the compounds of formula (I) as well as the salts thereof are able to form. Such solvates are, for example, hydrates, alcoholates and the like. Conversely the salt form can be converted by treatment with alkali into the free base form. Hereinafter the term "compounds of formula (I)" means the compound of formula (I) as well as the pharmaceutically acceptable acid addition salts thereof, unless otherwise mentioned.

Interesting compounds of formula (I) are the acid addition salts which are formed by treating the base form of the compound of formula (I) with hydrohalic acids or butanedioic acid.

Preferred compounds of formula (I) are 4-amino-5-chloro-2,3-dihydro-N-[1-(3-methoxypropyl)-4-piperidinyl]-7-benzofurancarboxamide monohydrochloride and 4-amino-5-chloro-2,3dihydro-N-[1-(3-methoxypropyl)-4-piperidinyl]-7-benzofurancarboxamide butane-dioate (1:1).

The compounds of formula (I) may be prepared according to procedures which are disclosed in EP-0,389,037-A and EP-0,445,862-A. A number of preparation alternatives are shown hereinunder.

In the following preparations, the reaction products may be isolated from the reaction mixture and, if necessary, further purified according to methodologies generally known in the art such as, for example, extraction, distillation, crystallization, trituration and chromatography.

The compounds of formula (I) can be prepared by N-alkylating an intermediate of formula (II) with an alkylating reagent of formula (III), wherein W is an appropriate leaving group such as a halo, e.g. chloro; or a sulfonyloxy leaving group, e.g. methanesulfonyloxy (mesylate) or a p-toluenesulfonyloxy (tosylate) in a reaction inert solvent such as a dipolar aprotic solvent, e.g. dimethyl formamide, in the presence of an appropriate base such as, for instance, triethylamine. A suitable catalyst such as potassium iodide may also be added to enhance the reaction rate.

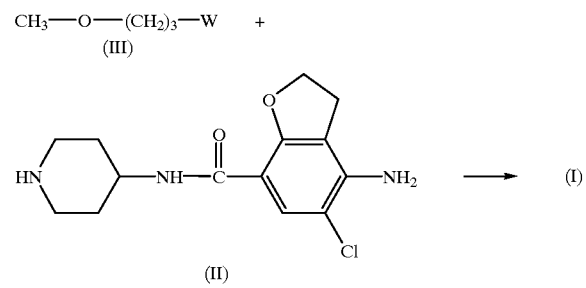

The compound of formula (I) may also be prepared by an N-acylation reaction of a carboxylic acid of formula (IV) or a reactive intermediate thereof and an amine of formula (V). Said N-acylation reaction may be performed by stifling the two reactants in a reaction-inert solvent, such as a chlorinated hydrocarbon, e.g. chloroform, or an aromatic hydrocarbon, e.g. toluene.

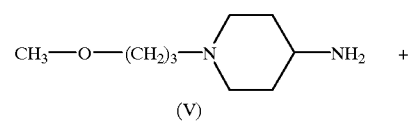

-continued

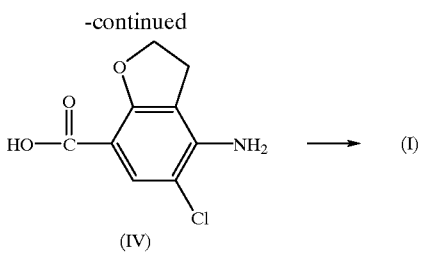

The above-mentioned intermediates are art-known or the preparation thereof is mentioned in EP-0,389,037-A and EP-0,445,862-A.

The compounds of formula (I) possess excellent intestinal motility stimulating properties. In particular the present compounds of formula (I) show significant motility enhancing effects on the small and large intestine. In other words the present compounds of formula (I) have enterokinetic properties. These properties are supported by the pharmacological examples described hereinunder. The present compounds of formula (I) enhance non-adrenergic non-cholinergic (NANC) excitation and the propulsion of faecal pellets through the large bowel. In addition, they accelerate gastric emptying and small intestinal contractile activity and have a facilitating effect on the cholinergic nerves. Said compounds are also devoid of 5-$HT_2$ or 5-$HT_3$ receptor antagonistic properties. Moreover, the present compounds also show in-vivo activity as is evidenced in the "Telemetric recording of colonic motility in conscious dogs" test.

In view of their useful enterokinetic enhancing properties the subject compounds may be formulated into various forms for administration purposes.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of their capability to stimulate the motility of the intestinal system and in particular their capacity to enhance the motility of the colon, the subject compounds are used to normalize or to improve the intestinal transit in subjects suffering from symptoms related to disturbed motility, e.g. a decreased peristalsis of the small and large intestine alone or in combination with delayed gastric emptying. In view of the utility of the compounds of the present invention there is provided a method of treating warm-blooded animals, including humans, suffering from motility disorders of the intestinal system, such as, for example, constipation, pseudo-obstruction, intestinal atony, post-operative intestinal atony, irritable bowel syndrome (IBS), and drug-induced delayed transit. In particular there is provided a method of treating large bowel motility disorders. The subject compounds may also be used to facilitate large bowel cleaning or to facilitate intubation and/or endoscopy. Said method comprises the systemic administration of an effective (small and large) intestinal stimulating amount of a compound of formula (I) to warm-blooded animals, including humans. Hence, the use of a compound of formula (I) as medicine is provided, and in particular the use of a compound of formula (I) for the manufacture of a medicine for treating conditions involving a disordered motility or transit of the small and large intestine.

In general it is contemplated that a therapeutically effective amount would be from about 0.001 mg/kg to about 10 mg/kg body weight, preferably from about 0.22 mg/kg to about 5 mg/kg body weight. A method of treatment may also include administering the active ingredient on a regimen of between two or four intakes per day.

EXPERIMENTAL PART

Example 1

In trichloromethane (135 ml) 4-amino-β-chloro-2,3-dihydro-7-benzofurancarboxylic acid (0.05 mol) (the preparation of which was described in EP-0,389,037-A) was suspended and cooled to ±5° C. N,N-diethylethanamine (0.05 mol) was added dropwise at a temperature below 10° C. Ethyl chloroformate (0.05 mol) was added dropwise and the reaction mixture was stirred for 40 min. while keeping the temperature below 10° C. The resulting mixture was added dropwise over a 20-min period to a solution of 1-(3-methoxypropyl)-4-piperidinamine (0.05 mol) in trichloromethane (35 ml). The cooling bath was removed and the reaction mixture was stirred for 150 min. Said mixture was washed with water (50 ml). The precipitate was filtered off over a glass filter and washed with water and CHCl$_3$. The filtrate was separated in it's layers. The separated organic layer was washed with water (50 ml)+a 50%

NaOH solution (1 ml), dried, filtered and the solvent was evaporated. The residue was stirred in 2-propanol (100 ml). This mixture was acidified with HCl/2-propanol (7.2 ml; 5.29 N). The mixture was stirred for 16 hours at room temperature and the resulting precipitate was filtered off, washed with 2-propanol (15 ml) and dried (vacuum; 50° C.), yielding 12.6 g (62%) of 4amino-5-chloro-2,3-dihydro-N-[1-(3-methoxypropyl)-4-piperidinyl]-7-benzofurancarboxamide monohydrochloride (comp. 1).

Example 2

A mixture of 4-amino-5-chloro-2,3-dihydro-N-(4-piperidinyl)-7-benzofurancarboxamide(0.01 mol), 1-chloro-3-methoxypropane (0.012 mol), N,N-diethylethanamine (2.1 ml) and KI (catalytic amount) in N,N-dimethylformamide (75 ml) was stirred overnight at 50° C. The reaction mixture was cooled. The solvent was evaporated. The residue was purified by column chromatography over silica gel (eluent: $CHCl_3m/(CH_3OH/NH_3)97/3$). The pure fractions were collected and the solvent was evaporated. The residue was dissolved in 2-propanol and converted into the hydrochloric acid salt (1:1) with HCl/2-propanol. The precipitate was filtered off and dried (vacuum; 80° C.), yielding 1.40 g (35%) of 4-amino-5-chloro-2,3-dihydro-N-[1-(3-methoxypropyl)-4-piperidinyl]-7-benzofurancarboxamide monohydrochloride (comp. 1).

Example 3

Reaction under $N_2$ flow. 4-Amino-5-chloro-2,3-dihydro-7-benzofurancarboxylic acid (0.18 mol) was dissolved in tetrahydrofuran (360 ml) and this solution was stirred and cooled to +3° C. 1,1'-Carbonylbis-1H-imidazole (0.18 mol) was added in one portion and cooling was stopped. The mixture was stirred for 75 minutes (became homogeneous after 30 minutes). A solution of 1-(3-methoxypropyl)-4-piperidinamine (0.18 mol) in tetrahydrofuran (90 ml) was added dropwise (exothermic temperature rise from 23° C. to 27° C). The reaction mixture was stirred for 24 hours. More 1,1'-Carbonylbis -1H-imidazole (0.0125 mol) was added and the reaction mixture was stirred for 75 minutes. More 1-(3-methoxypropyl)-4-piperidinamine (0.0125 mol) was added (in 10 ml THF). The resulting reaction mixture was stirred for 3 hours at room temperature, then for 2.5 hours at reflux temperature. Then, the mixture was stirred for 13 hours, allowing it to cool to room temperature. The solvent was evaporated. The residue was stirred for 8 hours in water (360 ml) and the precipitate was filtered off, washed with water, then dried (vacuum; 30° C.), yielding 62.9 g (95%) 4-amino-5-chloro-2,3-dihydro-N-[1-(3-methoxypropyl)-4-piperidinyl]-7-benzofurancarboxamide monohydrate; mp. 90.7° C. (comp. 2).

Example 4

Compound (2) (5 g, 0.0129 mol) was dissolved in warm ethanol (25 ml). A solution of (+)-(S)-lactic acid (1.45 g, 0.0135 mol) in ethanol (10 ml) was added. Under continuous stirring, crystallization started at 23° C. The mixture was stirred for 24 hours. The precipitate was filtered off, washed with ethanol (2 ml), then dried (vacuum; 55° C.; 72 hours), yielding 3.7 g (62%) of 4-amino-5-chloro-2,3-dihydro-N-[1-(3-methoxypropyl)-4-piperidinyl]-7-benzofurancarboxamide (+)-(S)-2-hydroxypropanoic acid salt (1:1); mp. 170.4° C. (comp. 3). Compound (2) (5 g, 0.0129 mol) was dissolved in warm ethanol (35 ml)/water (3.5 ml). Phosphoric acid (0.929 ml) was added and crystallization almost immediately resulted. The mixture was stirred for 24 hours at 23° C. The precipitate was filtered off, washed with ethanol (2 ml), then dried (vacuum; 55° C.; 72 hours), yielding 5.87 g (97.7%) 4-amino-5-chloro-2,3-dihydro-N-[1-(3-methoxypropyl)4-piperidinyl]-7-benzofurancarboxamide phosphoric acid salt (1:1); mp. 259.6° C. (comp. 4). Compound (2) (5 g, 0.0129 mol) was dissolved in warm ethanol (35 ml)/water (3.5 ml). A 48% hydrobromic acid solution (1.52 ml) was added and crystallization almost immediately resulted. The mixture was stirred for 24 hours at 13° C. The precipitate was filtered off, washed with ethanol (2 ml), then dried (vacuum; 55° C; 72 hours), yielding 5.4 g (93.2%) of 4-amino-5-chloro-2,3-dihydro-N-[1-(3-methoxypropyl)-4-piperidinyl]-7-benzofurancarboxamide.hydrobromide (1:1); mp. 280.1° C. (comp. 5). Compound (2) (5 g, 0.0129 mol) was dissolved in warm ethanol (25 ml). A solution of succinic acid (1.6 g) in ethanol (10 ml)/water (3.5 ml) was added. Upon scratching, crystallization resulted. The mixture was stirred for 24 hours at 23° C. The precipitate was filtered off, washed with ethanol (2 ml), then dried (vacuum; 55° C.; 72 hours), yielding 5.7 g (91%) of 4-amino-5-chloro-2,3-dihydro-N-[1-(3-methoxypropyl)-4-piperidinyl]-7-benzofurancarboxamide.butane-dioate (1:1); mp. 197.2° C. (comp. 6).

Example 5

Compound (2) (5 g, 0.0129 mol) was dissolved in ethanol (35 ml). Water (3.5 ml) was added. Sulfuric acid (0.75 ml) was added dropwise. The mixture was stirred for 24 hours at ±22° C. The precipitate was filtered off, washed with ethanol (2 ml), then dried (vacuum; 55-60° C; 72 hours), yielding 6.1 g (101%) of 4-amino-5-chloro-2,3-dihydro-N-[1-(3-methoxypropyl)-4-piperidinyl]-7-benzofurancarboxamide.sulfate (1:1); mp. 267.5° C. (comp. 7).

Compound (2) (5 g, 0.0129 mol) was dissolved in ethanol (35 ml). Water (3.5 ml) was added. Methanesulfonic acid (0.88 ml) was added dropwise. The mixture was stirred then dried (vacuum; 55-60° C.; 72 hours), yielding 6 g (100%) 4-amino-5-chloro-2,3 -dihydro-N-[1-(3-methoxypropyl)4-piperidinyl]-7-benzofurancarboxamide.methanesulfonic acid salt (1:1); mp. 286° C. (comp. 8). Compound (2) (5 g, 0.0129 mol) was dissolved in methylisobutyl ketone (35 ml), at 60–65° C. Acetic acid (0.8 ml) was added dropwise (temperature rise to 75° C.). Precipitation almost immediately resulted. The mixture was allowed to cool to room temperature. The mixture was stirred dissolved for 20 hours. The precipitate was filtered off, washed with ethanol (2 ml), then dried (vacuum; 55-60° C.; 72 hours), yielding 55 g (99%) of 4-amino-5-chloro-2,3-dihydro-N-[1-(3-methoxypropyl)4-piperidinyl]-7-benzofurancarboxamide.acetic acid salt (1:1); mp. 156.1° C. (comp. 9).

Pharmacological Examples

Example 6

Stimulation of non-adrenergic non-cholinergic nerves elicita relaxation followed by a contraction. The relaxation is mediated via a transmitter different from noradrenaline, nitric oxide or ATP. The contraction is mediated via a transmitter different from acetylcholine.

Dunkin-Hartley guinea pigs of either sex (350–600 g, not fasted) were killed by cervical dislocation followed by decapitation. The colon ascendens was removed and the lumen was cleansed by repeated washing with De Jalon solution. After carefully dissecting the mesentery, the colon ascendens was divided into 4 segments of 3 cm length. Each segment was mounted vertically in an organ bath containing 100 ml De Jalon solution. The organ bath was kept at 37° C. and gassed with a mixture of 95% oxygen and 5% carbondioxide. In order to block the α, β, and muscarinic receptors, phentolamine ($10^{-6}$ M), propanolol ($3\times10^{-7}$ M) and atropine ($3\times10^{-7}$ M) were added to the solution. Contractions were measured isometrically. The preparation was repeatedly stretched until a basal tension of 40 mN was obtained and allowed to stabilize for 45 to 60 minutes. Histamine ($3\times10^{-5}$ M) was added to the bath solution in order to obtain a maximal contraction. Transmural excitation was applied over the whole length of the colon strip by means of two platinum electrodes, the anode threaded through the lumen of the colon; the cathode in the bathing solution. The preparation was excited with rectangular square wave pulses (9 V, 1 ms/pulse) for 10 seconds every 5 minutes at different frequencies. Electrical stimulation resulted in a relaxation (=ON response) immediately followed by a contraction (=OFF response). Initially, the preparations were stimulated three times at 0.4 Hz in order to obtain a submaximal relaxation, followed by three stimuli at 1.5 Hz in order to obtain a submaximal contraction. Then the test compound was added to the bath fluid and again both stimuli (0.4 Hz and 1.5 Hz) were repeated three times.

At a concentration of $3\times10^{-7}$ M the test compound induced an increase of the OFF response of 100% of initial value.

Example 7

Dunkin-Hartley guinea pigs of either sex (350 g or more, not fasted) were killed by cervical dislocation followed by decapitation. The colon descendens was cut at ±5 cm from the rectum, cut and ligated at a length of ±40 cm and freed of adhering tissue. When there were at least 10 pellets in the colon, the tissue was transferred to a glass beaker containing 200 ml of Krebs-Henseleit solution, gassed with a mixture of 95% oxygen and 5% carbondioxide and maintained at 37° C. The solution contained either pure solvent or the test compound. The expelled pellets were counted and removed from the solution every 5 minutes during a maximum period of 60 minutes. The cumulative number of pellets expelled from the colon at every point was expressed as the percentage of the total number of pellets present in the entire colon at the start of the experiment. Time response curves were made by plotting the cumulative percentage of pellets expelled from the colon versus time. At a concentration of $3\times10^{-9}$ M of the present compound 80% of the initial amount of pellets was expelled within 10 minutes.

Example 8
Guinea Pig Ileum Coaxial Stimulation

Dunkin Hartley guinea-pigs of both sexes (body weight±500 g) were killed by cervical dislocation followed by decapitation. The ileum was removed and cleansed with warmed and oxygenated Krebs-Henseleit solution. Nonterminal, intact ileum segments, 4.5 cm long, of the guinea pig were vertically suspended with a preload of 1 g in 100 ml Krebs-Henseleit solution (37.5° C.), gassed with a mixture of 95% $O_2$ and 5% $CO_2$. Transmural excitation was applied over the whole length of the ileum segment by means of two platinum electrodes, the anode threaded through the lumen of the ileum, the cathode in the bathing solution. The preparation was excited with single rectangular stimili [1 msec; 0.1 Hz; submaximal response (current leading to 80% of maximal reponse)] from a programmable stimulator. Contractions were measured isometrically. During the stabilization period of 30 min, the strips were repeatedly stretched to a tension of 2 g, in order to obtain a steady state tension of 1 g. Before starting the electrical stimulation, a cumulative dose response curve of acetylcholine was given. The electrical stimulation was started at supramaximal current to determine the maximal amplitude of the twitch responses. When these responses were stable, a submaximal stimulation to obtain 80% of the maximal responses was given until the twitch responses were constant for at least 15 min, whereafter a single dose of the test compound was added to the bath fluid. The amplitude of the twitch response five minutes after the administration of the test compound is compared with the amplitude before the administration of the test compound. The present compound showed an increase of the amplitude of the twitch response of more than 5% at a concentration of $3.10^{-9}$ M.

What is claimed is:
1. A process of preparing a compound of formula

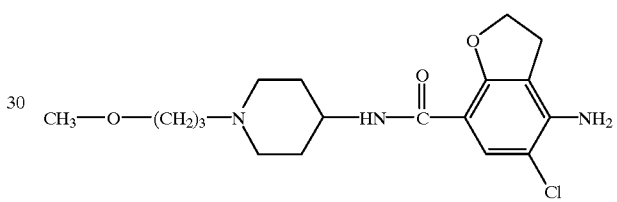

(I)

or a pharmaceutically acceptable acid addition salt thereof; wherein a) an intermediate of formula (II) is N-alkylated with an alkylating reagent of formula (III), wherein W is an appropriate leaving group in a reaction inert solvent in the presence of a suitable base;

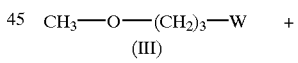

(III)

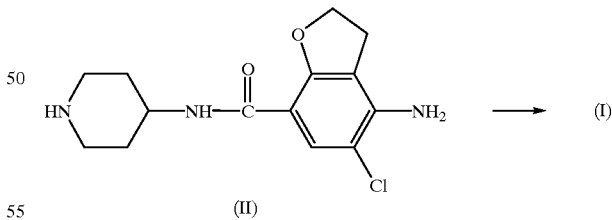

(II) → (I)

or b) an amine of formula (V) is N-acylated with a carboxylic acid of formula (IV)

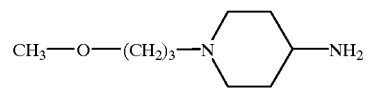

(V)

-continued

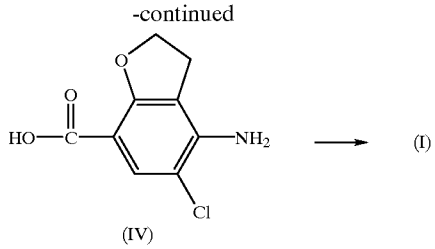

and, if desired, converting a compound of formula (I) into a therapeutically active non-toxic acid addition salt, or conversely, converting an acid addition salt into a free base form with alkali.

2. The process of claim 1, wherein the compound formula I is 4-amino-5-chloro-2,3-dihydro-N-[1-(3-methoxypropyl)-4-piperidinyl]-7-benzofurancarboxamide monohydrochloride.

3. The process of claim 1, wherein the appropriate leaving group is selected from a halo or a sulfonyloxy leaving group.

4. The process of claim 1, wherein the reaction inert solvent is a dipolar aprotic solvent.

5. The process of claim 1, wherein the suitable base is triethylamine.

* * * * *